| United States Patent [19] | [11] 3,995,323 |
| --- | --- |
| Shersher | [45] Dec. 7, 1976 |

[54] METHOD OF PREPARING BONE ENDOPROSTHESIS MODEL AND ENDOPROSTHESIS OF PROXIMAL FEMUR PREPARED WITH THE AID OF SAID MODEL

[76] Inventor: Yakov Isaevich Shersher, 1 Degtyarny proezd, 3, kv. 42, Saratov, U.S.S.R.

[22] Filed: Oct. 20, 1975

[21] Appl. No.: 624,119

[30] Foreign Application Priority Data

Oct. 31, 1974 U.S.S.R. .......................... 2069253

[52] U.S. Cl. ..................................... 3/1.913; 3/1.9;
128/92 C; 128/92 CA; 264/222; 264/DIG. 30
[51] Int. Cl.² ...................... A61F 1/24; B29C 1/02
[58] Field of Search ............................ 3/1.9–1.913,
3/1; 128/92 C, 92 CA, 92 G; 264/222, 223,
DIG. 30

[56] References Cited

UNITED STATES PATENTS

| 3,512,184 | 5/1970 | Grove | 3/1.912 |
| 3,662,405 | 5/1972 | Bortz et al. | 3/1.9 |
| 3,806,957 | 4/1974 | Shersher | 3/1.913 |
| 3,818,512 | 6/1974 | Shersher | 3/1.912 |

OTHER PUBLICATIONS

"A. Vitallium Replica Arthroplasty on the Shoulder," by F. J. Krueger, Surgery, Dec. 1951, pp. 1005–1011.

"Acrylic Prosthesis Replacing Lower End of the Femur for Benign Giant-Cell Tumor," by G. L. Kraft et al., The Journal of Bone & Joint Surgery, vol. 36–A, No. 2, Apr. 1954, pp. 368–374.

"Elbow Reconstruction with a New Prosthesis to Replace the Distal End of the Humerus," by J. S. Barr et al., The Journal of Bone & Joint Surgery, vol. 47–A, No. 7, Oct. 1965, pp. 1408–1413.

*Primary Examiner*—Ronald L. Frinks
*Attorney, Agent, or Firm*—Steinberg & Blake

[57] ABSTRACT

The present invention relates to methods of preparing a model of a bone endoprosthesis, and is most effectively used for the preparation of models of proximal femur in artificial hip joints.

The method of preparing said model consists in that a bone procured from a cadaver and corresponding to the bone to be subsequently replaced by a prosthesis is divided into two equal parts, the spongy tissue thereof is removed, thus forming a groove-like excavation in each part, thereafter the two parts are brought together in a fashion that the two grooves form a cavity serving as a casting mold wherein ventilation and filling orifices are made, wherethrough a self-hardening filling compound is poured, after which said mold is disassembled, and the model removed.

2 Claims, 3 Drawing Figures

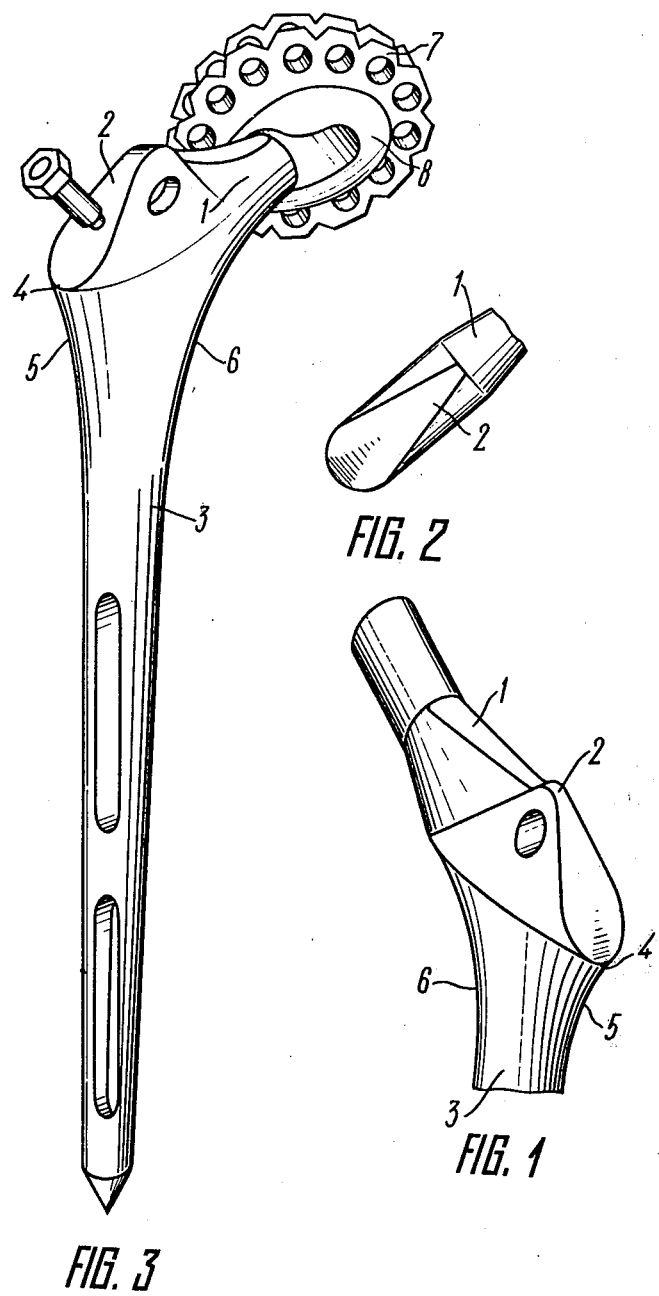

3,995,323

METHOD OF PREPARING BONE ENDOPROSTHESIS MODEL AND ENDOPROSTHESIS OF PROXIMAL FEMUR PREPARED WITH THE AID OF SAID MODEL

The present invention relates to artificial joints for surgical intra-articular prosthetic replacement, and, more precisely, to preparing models of bone endoprostheses and to endoprostheses of the proximal femur, prepared with the aid of said models.

The proposed method can be most effectively employed in preparing models of endoprostheses of the proximal femur in artificial hip joints, as well as in preparing bone models intended for the preparation of knee joints and shoulder joints.

At present, endoprosthetic replacement of various joints is the most effective method of restoration of the lost mobility thereof. This is particularly true in the case of the hip joint.

As is well known from experience good results of the surgical procedure are ensured, predominantly, by a firm fixation of the prosthesis to the bones.

In some cases, the fixation of prostheses is effected by cementation. This, however, results in a number of severe complications (cracking of the cement, loss of adherence thereof to the bone, sharp blood pressure drop during the cementation). Alternately, the prostheses are fixed by way of mechanical connection thereof to the bone. In case of a mechanical fixation, the endoprosthesis is usually prepared in accordance with a technology that permits obtaining an external shape only approximately resembling that of the bone, without precisely matching the shape and size of said prosthesis with the inner surfaces of the bone. Hence, such technology entails a discrepancy between the outer shape and size of the prosthetic elements to serve for the fixation to the bones, and the shape and size of the inner surface of said bone. This necessitates the removal of substantial portions of pathologically unchanged bone in the patient so as to match the size thereof with the size and shape of the endoprosthesis.

It is an object of the present invention to eliminate the above disadvantages.

Another object of the invention is to provide a method of preparing a model of a bone endoprosthesis such that would reproduce the anatomic shape and size of the inner surface of the bone to be replaced by said prosthesis as closely as possible.

Yet another object of the invention is to provide a method of preparing a model of a bone endoprosthesis that would ensure maximum preservation of the patient's bone tissue.

It is a further object of the invention to provide a method of preparing a model of a bone endoprosthesis that would ensure firm mechanical fixation thereof to the bone.

These and other objects of the invention are attained by that, in accordance with the present invention, the bone procured from a cadaver and corresponding to the bone to be replaced by an endoprosthesis is divided into two longitudinal, practically equal parts, the spongy tissue thereof is removed, thus forming a groove-like excavation in each part, thereafter the two parts are brought together in a fashion that the two grooves form a cavity serving as a casting mold, wherein ventilation and filling orifices are made, wherethrough a self-hardening filling compound is poured, after which said mold is disassembled, and the model removed.

Such a method permits preparing a model of a bone endoprosthesis whose outer shape reproduces precisely the inner surface of the bone upon the removal of the spongy tissue therefrom. The exact fitness of the prosthesis and the bone ensures a firm fixation thereof, and, which is of paramount importance, a possibility of maximum preservation of the patient's bone.

Further, in accordance with the invention, an endoprosthesis of the proximal femur in an artificial hip joint, made on the basis of a model prepared according to the above method, has an intertrochanteric part with a compound profile in the cross section having, in the portion of the transition of the above part into the neck of the femur, the shape of a triangle, with the base thereof being convexed outwardly, and in the portion adjacent to the base of the greater trochanter that of a frustum which base smoothly proceeds into a shaft for intraosseous introduction, the two opposite surfaces of the shaft having the shape of conics the convexities thereof facing one another.

The invention will be further understood from the following description of an exemplary embodiment thereof with reference to the accompanying drawings, wherein:

FIG. 1 shows an endoprosthesis of the proximal femur;

FIG. 2 is a top plan view of FIG. 1;

FIG. 3 presents a general view of an artificial hip joint employing the endoprosthesis presented in FIG. 1.

The proposed method of preparing a bone endoprosthesis model consists in the following. A bone procured from a cadaver and corresponding to the bone to be replaced is selected. Thereafter, the bone is split longitudinally into two, practically equal parts. Then, the spongy tissue is removed therefrom, thus forming a groove-like excavation in each part.

This done, both parts are brought together so as to form a cavity that serves as a casting mold.

Two orifices are made in said casting mold: a ventilation orifice and a filling orifice wherethrough a self-hardening filling compound is poured. Thereafter the casting mold is disassembled, and the model removed. The portions to be preserved in the patient during surgery are then removed from said model.

FIG. 1 shows an endoprosthesis of the proximal femur prepared on the basis of said model made by the above method. The endoprosthesis of FIG. 1 comprises a neck 1, one end of which is free for fixing thereon the head of an artificial hip joint, the other end thereof passing into an intertrochanteric part 2, that, in turn, smoothly passes into a shaft 3 for intraosseous insertion. The intertrochanteric part 2 has a compound profile that has, in the portion of transition of said part into the neck 1, the shape of a triangle with a base convexed outwardly, and in the portion corresponding to a base of the greater trochanter 4 on the bone, that of a frustum which base smoothly passes into the shaft 3 for intraosseous insertion. In the portion of transition from the intertrochanteric portion into the shaft, two opposite surfaces 5 and 6 of said shaft have the shape of conics, the convexities thereof facing each other.

Such a shape permits preserving the intertrochanteric zone of the femur, saving to the maximum the tissue of the greater trochanter, severed during surgery, and firmly fixing the prosthesis mechanically.

The endoprosthesis of the proximal femur, as shown in FIG. 1, can be obtained on the basis of a model made in accordance with the above method by way of removing, from the intertrochanteric part, the portion corresponding to the greater trochanter of the bone. Said removal is accomplished, in fact, perpendicularly to the axis connecting the apex of the greater and lesser trochanters.

Thereafter, the portions located oppositely on the external surface of the intertrochanteric part 2 and having the shape of triangles with their apices facing each other are removed. The resulting cross-section of the intertrochanteric part has a compound profile, as described above and seen in FIG. 2.

It should be emphasized that the following requirements have to be complied with in the preparation of said endoprosthesis: the inner surface of the casting mold to be treated with some material preventing sticking of the model to the bone, the temperature of the self-hardening filling compound to be that of the ambient air, i.e. about 18°–20° C, the self-hardening filling compound to be a material with low deformation properties, prompt hardening and ability to fill the whole space of the casting mold. Plaster of Paris is recommended as such material. Other materials, however, having the above mentioned properties can be employed as well.

FIG. 3 presents an artificial hip joint containing an artificial cotyloid cavity 7, a head 8, a proximal femur prepared in accordance with the above method and having the above shape, and the shaft 3 for intraosseous insertion.

What is claimed is:
1. A method of preparing a model of a bone endoprosthesis comprising the following steps: dividing the bone procured from a cadaver and corresponding to the bone to be replaced by an endoprosthesis into two, practically equal parts; removing the spongy tissue therefrom, thus forming groove-like excavations in each part; bringing together the above parts so as to form a cavity of said grooves, intended as a casting mold; making a ventilation and a filling orifices in said casting mold wherethrough a self-hardening filling compound is poured, and subsequently disassembling the casting mold and removing the model therefrom.

2. An endoprosthesis of the proximal femur in an artificial hip joint prepared on the basis of a model made in accordance with the method of preparing a model of a bone endoprosthesis as defined in claim 1, comprising a neck, an intertrochanteric part with an element corresponding to the greater trochanter, and a shaft for intraosseous insertion, said intertrochanteric part having a compound profile in the cross-section which has in the portion of transition thereof into said neck, the shape of a triangle with a base convexed outwardly and, in the portion adjacent to the base of the greater trochanter, that of a frustum, the base thereof smoothly into said shaft having, in said portion, two opposite surfaces shaped in the form of conics, the convexities thereof facing each other.

* * * * *